(12) United States Patent
Kim et al.

(10) Patent No.: US 11,504,696 B2
(45) Date of Patent: *Nov. 22, 2022

(54) SUPER ABSORBENT POLYMER

(71) Applicant: LG Chem, Ltd., Seoul (KR)

(72) Inventors: Kyu Pal Kim, Daejeon (KR); Gi Cheul Kim, Daejeon (KR); Ki Hyun Kim, Daejeon (KR); Seul Ah Lee, Daejeon (KR); Sang Gi Lee, Daejeon (KR)

(73) Assignee: LG Chem, Ltd.

( * ) Notice: Subject to any disclaimer, the term of this patent is extended or adjusted under 35 U.S.C. 154(b) by 373 days.

This patent is subject to a terminal disclaimer.

(21) Appl. No.: 16/632,789

(22) PCT Filed: Aug. 14, 2018

(86) PCT No.: PCT/KR2018/009352
§ 371 (c)(1),
(2) Date: Jan. 21, 2020

(87) PCT Pub. No.: WO2019/050183
PCT Pub. Date: Mar. 14, 2019

(65) Prior Publication Data
US 2021/0031169 A1  Feb. 4, 2021

(30) Foreign Application Priority Data
Sep. 5, 2017  (KR) .................. 10-2017-0113133

(51) Int. Cl.
| B01J 20/26 | (2006.01) |
| B01J 20/28 | (2006.01) |
| B01J 20/30 | (2006.01) |
| A61L 15/60 | (2006.01) |
| A61L 15/24 | (2006.01) |

(52) U.S. Cl.
CPC ............ B01J 20/267 (2013.01); A61L 15/24 (2013.01); A61L 15/60 (2013.01); B01J 20/28011 (2013.01); B01J 20/3064 (2013.01)

(58) Field of Classification Search
None
See application file for complete search history.

(56) References Cited

U.S. PATENT DOCUMENTS

| 4,734,478 | A | 3/1988 | Tsubakimoto et al. |
| 5,856,370 | A | 1/1999 | Chmelir |
| 6,284,362 | B1 | 9/2001 | Takai et al. |
| 7,163,966 | B2 | 1/2007 | Joy et al. |
| 2005/0137546 | A1* | 6/2005 | Joy ................... A61L 15/60 604/368 |
| 2007/0088093 | A1 | 4/2007 | Joy et al. |
| 2009/0169891 | A1 | 7/2009 | Higashimoto et al. |
| 2009/0191408 | A1 | 7/2009 | Tian et al. |
| 2011/0204289 | A1 | 8/2011 | Higashimoto et al. |
| 2012/0001122 | A1* | 1/2012 | Wattebled ............. C08F 2/44 252/194 |
| 2013/0096000 | A1* | 4/2013 | Tian ................. B01J 20/267 502/402 |
| 2013/0110067 | A1* | 5/2013 | Carlucci ............. A61L 15/22 604/370 |
| 2016/0361703 | A1* | 12/2016 | Jang ................. C08J 3/075 |
| 2017/0166670 | A1 | 6/2017 | Matsumoto et al. |
| 2018/0079847 | A1 | 3/2018 | Lee et al. |
| 2020/0188876 | A1* | 6/2020 | Kim .................. C08J 9/141 |
| 2020/0324270 | A1* | 10/2020 | Yoon ................. C08J 9/32 |
| 2021/0023529 | A1* | 1/2021 | Lee .................. C08J 3/075 |
| 2021/0079141 | A1* | 3/2021 | Yoon ................. C08J 9/28 |
| 2021/0094017 | A1* | 4/2021 | Choi ................. C08K 9/10 |

FOREIGN PATENT DOCUMENTS

| CN | 102361653 A | 2/2012 |
| CN | 102858816 A | 1/2013 |
| EP | 0083022 A2 | 7/1983 |
| JP | 2007514833 A | 6/2007 |
| JP | 2007270157 A | 10/2007 |
| JP | 2009051952 A | 3/2009 |
| JP | 2009280667 A | 12/2009 |
| JP | 4829185 B2 | 12/2011 |
| JP | 2012522880 A | 9/2012 |
| JP | 5336704 B2 | 11/2013 |
| JP | 2016508167 A | 3/2016 |
| JP | 2016056353 A | 4/2016 |
| KR | 20080091488 A | 10/2008 |
| KR | 20080094929 A | 10/2008 |
| KR | 20120043165 A | 5/2012 |
| KR | 20140066247 A | 5/2014 |
| KR | 20160056326 A | 5/2016 |
| KR | 20160076422 A | 6/2016 |
| KR | 20160147520 A | 12/2016 |
| KR | 20160149239 A | 12/2016 |
| KR | 20170002468 A | 1/2017 |
| WO | 1999003577 A1 | 1/1999 |
| WO | 2005063313 A1 | 7/2005 |
| WO | 2007091960 A1 | 8/2007 |
| WO | 2009097420 A2 | 8/2009 |

OTHER PUBLICATIONS

Elsevier; UV Coatings: Basics, Recent Developments and New Applications; Dec. 21, 2006, p. 115.
Frederic L. Buchholz et al., "Modern Superabsorbent Polymer Technology", 1998, 50 pages.
International Search Report for Application No. PCTKR2018009352 dated Jan. 4, 2019, 3 pages.
Odian; Principle of Polymerization, second edition; 1981, p. 203.

* cited by examiner

Primary Examiner — Joseph D Anthony
(74) Attorney, Agent, or Firm — Lerner, David, Littenberg, Krumholz & Mentlik, LLP

(57) ABSTRACT

The present invention relates to a super absorbent polymer. The super absorbent polymer exhibits excellent initial absorption capacity, and thus can provide a sanitary material such as a diaper or a sanitary napkin which can quickly absorb body fluids and impart a dry and soft touch feeling.

8 Claims, No Drawings

SUPER ABSORBENT POLYMER

CROSS-REFERENCE TO RELATED APPLICATION(S)

The present application is a national phase entry under 35 U.S.C. § 371 of International Application No. PCT/KR2018/009352, filed Aug. 14, 2018, which claims priority from Korean Patent Application No. 10-2017-0113133, filed on Sep. 5, 2017, the disclosures of which are incorporated herein by reference in their entirety.

TECHNICAL FIELD

The present invention relates to a super absorbent polymer exhibiting excellent initial absorption capacity.

BACKGROUND

Technical Field

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for production of hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of sanitary materials such as diapers or sanitary napkins. Recently, fast-drying capability is required for sanitary materials such as diapers and sanitary napkins. In order to satisfy these requirements, the surface area of the super absorbent polymer is sufficiently large and thus it is necessary to exhibit excellent initial absorption capacity.

The super absorbent polymer is produced using methods such as suspension polymerization and solution polymerization. Since the suspension polymerization can produce a super absorbent polymer having a large surface area, it can be usefully used for sanitary materials requiring fast-drying capability. However, since the suspension polymerization uses an organic solvent, there is a problem that mass production is difficult, and the production cost increases due to an additional step of recycling the organic solvent. Since the solution polymerization does not use an organic solvent, it is possible to economically produce a super absorbent polymer in a mass, but there is a problem that by pulverizing the polymer, amorphous particles are obtained and thus a super absorbent resin having a relatively small surface area is obtained.

Thus, a technique of producing a super absorbent polymer through the solution polymerization, but using a carbonate foaming agent for widening the surface area of the super absorbent polymer has been introduced. However, a super absorbent polymer exhibiting sufficient initial absorption capacity has not been developed yet.

Technical Problem

The present invention provides a super absorbent polymer exhibiting excellent initial absorption capacity.

Technical Solution

Hereinafter, a super absorbent polymer and a method for preparing the same according to specific embodiments of the present invention will be described in detail.

According to one embodiment of the present invention, there is provided a super absorbent polymer comprising: a base polymer powder including a cross-linked polymer obtained by crosslinking polymerization of a water-soluble ethylenically unsaturated monomer having an acidic group of which at least a part is neutralized in the presence of an encapsulated foaming agent; and a surface cross-linked layer that is further cross-linked from the cross-linked polymer and is formed on the base polymer powder, wherein an initial absorption capacity calculated according to the following Calculation Formula 1 is at least 30 g/g.

Initial absorption capacity (g/g)= $[W_2(g)-W_1(g)]/W_0(g)-1$  [Calculation Formula 1]

in Calculation Formula 1, $W_0(g)$ is an initial weight (g) of the polymer, $W_1(g)$ is a weight of a nonwoven fabric-made empty bag not containing the polymer, which is measured after immersing the empty bag not containing the polymer in a physiological saline solution at 36° C. for 1 minute, and then dehydrating the same by gravity for 1 minute, and $W_2(g)$ is a weight of a nonwoven fabric-made bag containing the polymer, which is measured after immersing and absorbing the bag containing the polymer in a physiological saline solution at 36° C. for 1 minute, and then dehydrating the same by gravity for 1 minute.

Since the super absorbent polymer has a particle shape, the individual particles constituting the super absorbent polymer as used herein may be referred to as polymer particles.

The super absorbent polymer is produced using methods such as suspension polymerization and solution polymerization. Since the suspension polymerization can produce a super absorbent polymer having a large surface area, it can be usefully used for sanitary materials requiring fast-drying capability. However, since the suspension polymerization uses an organic solvent, there is a problem that mass production is difficult, and the production cost increases due to an additional step of recycling the organic solvent. Since the solution polymerization does not use an organic solvent, it is possible to economically produce a super absorbent polymer in a mass, but there is a problem that by pulverizing the polymer, amorphous particles are obtained and thus a super absorbent resin having a relatively small surface area is obtained.

However, as a result of experiments made by the present inventors, it has been found that, when a specific encapsulated foaming agent is used during the preparation of a super absorbent polymer even if the solution polymerization is employed, the super absorbent polymer has a sufficiently large surface area and thus exhibits excellent initial absorption capacity. As a result, such a super absorbent polymer can provide a sanitary material such as a diaper or a sanitary napkin which can quickly absorb body fluids and impart a dry and soft touch feeling.

Specifically, the super absorbent polymer may have an initial absorption capacity calculated according to Calculation Formula 1 of 30 g/g or more, 35 g/g or more, 40 g/g or more, or 45 g/g or more. The method of measuring the initial absorption capacity is described in detail in Test Examples described below, and the upper limit of the initial absorption capacity is not particularly limited and for example, it may be 100 g/g or less, or 70 g/g or less, or 60 g/g or less.

Further, the super absorbent polymer may have a centrifuge retention capacity (CRC) for a physiological saline solution of 30 to 45 g/g or 35 to 40 g/g. A method of measuring the centrifuge retention capacity for a physiological saline solution is described in detail in Test Examples described later.

The super absorbent polymer according to one embodiment of the invention may comprise a base polymer powder including a cross-linked polymer obtained by crosslinking polymerization of a water-soluble ethylenically unsaturated monomer having an acidic group of which at least a part is neutralized in the presence of an encapsulated foaming agent; and a surface cross-linked layer that is further cross-linked from the cross-linked polymer and is formed on the base polymer powder.

The encapsulated foaming agent may be adjusted to have an average diameter measured before being expanded, for example, from 5 to 50 μm, from 5 to 30 μm, from 5 to 20 μm, or from 7 to 17 μm, and thus polymer particles in which large pores are uniformly formed can be produced.

The encapsulated foaming agent may have a structure including a core containing hydrocarbon and a shell surrounding the core and formed of a thermoplastic resin. Because such an encapsulated forming agent can be allowed to expand to a desired size, it is used during the preparation of the super absorbent polymer, thereby enabling the super absorbent polymer to exhibit excellent initial absorption capacity.

When the pores of a proper size are formed on the surface of the polymer particle, the initial absorption capacity of the super absorbent polymer can be remarkably improved. Specifically, when the particle diameter of the polymer particle is 300 to 425 μm, the pore size is suitably about 20 to 200 μm. When the above-described encapsulated foaming agent is used, polymer particles having pores of this size on the surface can be produced. In order to mass-produce polymer particles having pores of the above-mentioned size, it is necessary to grasp the expansion characteristics of the encapsulated foaming agent. However, since the form in which the foaming agent encapsulated in the super absorbent polymer is foamed may vary depending on the preparation conditions of the super absorbent polymer, it is difficult to define it in one form. Thus, by foaming the encapsulated foaming agent in air and confirming the expansion ratio and size, it can be confirmed whether or not it is suitable for forming polymer particles having pores of a proper size.

Specifically, the encapsulated foaming agent is coated onto a glass Petri dish, and then a heat is applied in air for 10 minutes to foam the encapsulated foaming agent. In this case, if the encapsulated foaming agent exhibits a maximum expansion ratio in air of 3 to 15 times, 5 to 15 times, or 8.5 to 10 times, it is suitable for mass production of polymer particles having large pores.

Further, the encapsulated foaming agent should exhibit the maximum expansion size in air of 190 μm or less so that polymer particles having pores of a proper size can be produced in a mass. Specifically, if the encapsulated foaming agent exhibits a maximum expansion size in air of 20 to 190 μm, 50 to 190 μm, 70 to 190 μm, or 75 to 190 μm, it is suitable for mass production of polymer particles having pores of a proper size.

The maximum expansion ratio and the maximum expansion size of the encapsulated foaming agent in air are described in detail in Preparation Examples described later.

The hydrocarbon constituting the core of the encapsulated foaming agent may be at least one selected from the group consisting of n-propane, n-butane, iso-butane, cyclobutane, n-pentane, iso-pentane, cyclopentane, n-hexane, iso-hexane, cyclohexane, n-heptane, iso-heptane, cycloheptane, n-octane, iso-octane, and cyclooctane. Among them, hydrocarbons having 3 to 5 carbon atoms (n-propane, n-butane, iso-butane, cyclobutane, n-pentane, iso-pentane, cyclopentane) are suitable for forming pores of the aforementioned size, and iso-butane is most suitable.

Further, the thermoplastic resin constituting the shell of the encapsulated foaming agent may be a polymer formed from at least one monomer selected from the group consisting of (meth)acrylate, (meth)acrylonitrile, aromatic vinyl, vinyl acetate, vinyl halide and vinylidene halide. Among them, copolymers of (meth)acrylate and (meth)acrylonitrile are most suitable for realizing the initial absorption capacity in the above-mentioned range.

The encapsulated foaming agent may contain 10 to 30% by weight of hydrocarbon based on the total weight of the encapsulated foaming agent. Within such range, it is possible to provide the super absorbent polymer exhibiting the initial absorption capacity in the above-mentioned range.

Hereinafter, the method for preparing the super absorbent polymer of one embodiment will be described in more detail.

The super absorbent polymer according to one embodiment may be produced through the steps of: performing a crosslinking polymerization of a water-soluble ethylenically unsaturated monomer having an acidic group of which at least a part is neutralized in the presence of an encapsulated foaming agent to form a hydrogel polymer; drying, pulverizing and classifying the hydrogel polymer to form a base polymer powder; and further cross-linking the surface of the base polymer powder in the presence of a surface crosslinking agent to form a surface cross-linked layer.

Since the encapsulated foaming agent has been previously described in detail, a detailed description thereof will be omitted here.

The water-soluble ethylenically unsaturated monomer may include at least one selected from the group consisting of anionic monomers of (meth)acrylic acid, maleic acid, maleic anhydride, fumaric acid, crotonic acid, itaconic acid, sorbic acid, vinylphosphonic acid, vinyl sulfonic acid, allylsulfonic acid, 2-(meth)acryloylethanesulfonic acid, 2-(meth)acryloyloxyethanesulfonic acid, 2-(meth)acryloylpropanesulfonic acid, and salts thereof; non-ionic, hydrophilic group-containing monomers of (meth)acrylamide, N-substituted (meth)acrylamide, 2-hydroxyethyl(meth)acrylate, 2-hydroxypropyl(meth)acrylate, methoxypolyethylene glycol(meth)acrylate or polyethylene glycol (meth)acrylate; and amino group-containing unsaturated monomers of (N,N)-dimethylaminoethyl(meth)acrylate or (N,N)-dimethylaminopropyl(meth)acrylamide, and their quaternarized product.

The term "water-soluble ethylenically unsaturated monomer having an acidic group of which at least a part is neutralized" as used herein means that a monomer having an acidic group is contained in the water-soluble ethylenically unsaturated monomer and at least a part of the acidic group in the monomer having an acidic group is neutralized.

In particular, the water-soluble ethylenically unsaturated monomer is composed of a monomer (a salt of an anionic monomer) in which at least a part has neutralized an acidic group contained in the anionic monomer.

More specifically, as the water-soluble ethylenically unsaturated monomer, acrylic acid or a salt thereof may be used. In the case of using acrylic acid, at least a part of the acid can be neutralized and used. The use of such monomer makes it possible to produce a super absorbent polymer having superior physical properties. As an example, when an alkali metal salt of acrylic acid is used as the water-soluble ethylenically unsaturated monomer, the acrylic acid may be neutralized with a neutralizing agent such as caustic soda (NaOH) and used. In this case, the degree of neutralization of the acrylic acid may be adjusted to about 50 to 95 mol %, or about 60 to 85 mol %. Within this range, it is possible to provide a super absorbent polymer having excellent centrifuge retention capacity without fear of precipitation during neutralization.

In the monomer mixture including the water-soluble ethylenically unsaturated monomer, the concentration of the water-soluble ethylenically unsaturated monomer may be about 20 to about 60% by weight, or about 25 to about 50% by weight, with respect to the entire monomer mixture including the respective raw materials, polymerization initiators and solvents, etc. described below, and it may be controlled to an appropriate concentration in consideration of the polymerization time and reaction conditions, etc. However, when the concentration of the monomer is excessively low, the yield of the super absorbent polymer may be lowered, which may cause a problem in economic efficiency. Conversely, when the concentration is excessively high, a part of the monomer may precipitate or the pulverization efficiency may be lowered upon pulverization of the polymerized hydrogel polymer, which may cause a problem in the process, and the physical properties of the super absorbent polymer may be deteriorated.

In the step of forming the hydrogel polymer, an internal crosslinking agent may be used for crosslinking polymerization of the water-soluble ethylenically unsaturated monomer. The internal crosslinking agent is composed of a compound containing two or more crosslinkable functional groups in the molecule. The internal crosslinking agent may contain a carbon-carbon double bond as a cross-linkable functional group for smooth crosslinking polymerization reaction of the water-soluble ethylenically unsaturated monomer. More specific examples of the internal crosslinking agent may include at least one selected from the group consisting of diethylene glycol diacrylate, triethylene glycol diacrylate, glycerin diacrylate, glycerin triacrylate, unmodified or ethoxylated trimethylolpropane triacrylate (TMPTA) and hexanediol diacrylate.

The internal crosslinking agent can be contained at a concentration of about 0.01 to about 2% by weight with respect to the monomer mixture, and thus a cross-linked polymer exhibiting a fast absorption rate while having excellent centrifuge retention capacity and absorbency under pressure can be formed.

In addition, the monomer mixture may further include a polymerization initiator commonly used for the preparation of a super absorbent polymer.

Specifically, the polymerization initiator can be properly selected depending on the polymerization method. In the case of a thermal polymerization, a thermal polymerization initiator is used, and in the case of a photo-polymerization, a photo-polymerization initiator is used. Further, in the case of a mixed polymerization method (a method using both heat and light) is used, all of the thermal polymerization initiator and the photo-polymerization initiator can be used. However, even in the case of the photo-polymerization method, because a certain amount of heat is generated by the ultraviolet irradiation or the like and heat is generated to some degree according to the progress of the exothermic polymerization reaction, a thermal polymerization initiator may be additionally used.

The photo-polymerization initiator can be used without any limitation in its constitution as long as it is a compound capable of forming a radical by a light such as ultraviolet rays.

The photo-polymerization initiator, for example, may include at least one selected from the group consisting of a benzoin ether, a dialkyl acetophenone, a hydroxyl alkylketone, a phenyl glyoxylate, a benzyl dimethyl ketal, an acyl phosphine, and an α-aminoketone. Meanwhile, specific examples of the acyl phosphine may include diphenyl(2,4,6-trimethylbenzoyl) phosphine oxide, phenyl bis(2,4,6-trimethylbenzoyl)phosphine oxide, ethyl(2,4,6-trimethylbenzoyl)phenylphosphinate, and the like. More various photo-polymerization initiators are well disclosed in "UV Coatings: Basics, Recent Developments and New Application" written by Reinhold Schwalm, (Elsevier, 2007), p 115, however the photo-polymerization initiator is not limited to the above-described examples.

The photo-polymerization initiator may be included in a concentration of about 0.0001 to about 2.0% by weight with respect to the monomer mixture. When the concentration of the photo-polymerization initiator is excessively low, the polymerization rate may become slow, and when the concentration of the photo-polymerization initiator is excessively high, the molecular weight of the super absorbent polymer may become small and its physical properties may become uneven.

Further, as the thermal polymerization initiator, at least one selected from the group consisting of persulfate-based initiator, azo-based initiator, hydrogen peroxide and ascorbic acid can be used. Specifically, examples of the persulfate-based initiators include sodium persulfate ($Na_2S_2O_8$), potassium persulfate ($K_2S_2O_8$), ammonium persulfate (($NH_4$)$_2$$S_2O_8$) and the like, and examples of the azo-based initiator include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane]dihydrochloride, 4,4-azobis-(4-cyanovaleric acid) and the like. More various thermal polymerization initiators are well disclosed in "Principle of Polymerization" written by Odian, (Wiley, 1981), p 203, however the thermal polymerization initiator is not limited to the above-described examples.

The thermal polymerization initiator can be included in the concentration of about 0.001 to about 2.0% by weight with respect to the monomer mixture. When the concentration of the thermal polymerization initiator is excessively low, the additional thermal polymerization hardly occurs and thus effects due to the addition of the thermal polymerization initiator may be insignificant, and when the concentration of the thermal polymerization initiator is excessively high, the molecular weight of the super absorbent polymer becomes small and the physical properties may become uneven.

Meanwhile, the above-mentioned monomer mixture may contain the encapsulated foaming agent in the concentration of about 0.05 to about 5% by weight, or about 0.1 to about 3% by weight, with respect to the entire monomer mixture. Thereby, it is possible to appropriately obtain a super absorbent polymer that satisfies various physical properties such as the above-described initial absorption capacity.

In addition, the above-mentioned monomer mixture may further include additives such as a thickener, a plasticizer, a preservation stabilizer, an antioxidant, a surfactant, and so on, as needed.

The above-mentioned raw materials such as the water-soluble ethylenically unsaturated monomer, the encapsulated foaming agent, the internal crosslinking agent, the polymerization initiator, and the additives may be prepared in the form of a solution that is dissolved in a solvent.

In this case, the solvent can be used without limitation in its constitution as long as it can dissolve the above-mentioned components. For example, one or more solvents selected from the group consisting of water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butylolactone, carbitol, methylcellosolve acetate, and N,N-dimethyl acetamide, and so on may be used alone or in combination with each other.

The solvent may be included in a residual amount of excluding the above-described components from the total weight of the monomer mixture.

Meanwhile, the method for forming a hydrogel polymer by the thermal polymerization, photo-polymerization or mixed polymerization of such a monomer composition is not particularly limited in terms of its constitution as long as it is a polymerization method commonly used in the art.

Specifically, the polymerization process may be largely classified into a thermal polymerization and a photo-polymerization depending on a polymerization energy source. The thermal polymerization may be typically carried out in a reactor like a kneader equipped with agitating spindles. In this case, a polymerization temperature of the monomer mixture may be controlled from about 30° C. to 110° C., thereby forming a hydrogel polymer having an appropriate crosslinking structure. Means for achieving the polymerization temperature within the above-described range is not particularly limited. Heating may be performed by providing a heating medium to the reactor or by directly providing a heat source. The type of the heating medium applicable may be a heated fluid such as steam, hot air, hot oil, etc., but is not limited thereto. Further, the temperature of the heating medium provided may be properly selected in consideration of the means of the heating medium, the temperature raising speed, and the temperature raising target temperature. Meanwhile, a heating method using electricity or a heating method using gas may be used as the heat source provided directly, but the heat source is not limited to the above-described examples.

Meanwhile, in the case of the photo-polymerization, it can be carried out in a reactor equipped with a movable conveyor belt, but the above-mentioned polymerization method is merely an example, and the present invention is not limited to the above-mentioned polymerization method.

As an example, when the thermal polymerization is carried out in a reactor such as a kneader equipped with a stirring spindle, the hydrogel polymer that is discharged from the outlet of the reactor can be obtained. The hydrogel polymer thus obtained may have a size of several centimeters to several millimeters, according to the shape of the stirring spindle equipped in the reactor. Specifically, the size of the obtained hydrogel polymer may vary according to the concentration of the monomer mixture injected thereto, the injection speed, or the like.

Further, as described above, when the photo-polymerization is carried out in a reactor equipped with a movable conveyor belt, the obtained hydrogel polymer may be usually a sheet-like hydrogel polymer having a width of the belt. In this case, the thickness of the polymer sheet may vary depending on the concentration and the injection speed of the monomer mixture to be injected thereto, but usually, it is preferable to feed the monomer mixture so that a sheet-like polymer having a thickness of about 0.5 to about 10 cm can be obtained. When the monomer mixture is fed to such an extent that the thickness of the sheet-like polymer becomes too thin, it is undesirable because the production efficiency is low, and when the thickness of the sheet-like polymer is greater than 10 cm, the polymerization reaction cannot be evenly carried out over the entire thickness because of the excessive thickness.

The polymerization time of the monomer mixture is not particularly limited, and may be controlled from about 30 seconds to 60 minutes.

The hydrogel polymer obtained by the above-mentioned method may have a water content of about 30 to about 80% by weight. Meanwhile, the "water content" as used herein means a weight occupied by moisture with respect to a total amount of the hydrogel polymer, which may be the value obtained by subtracting the weight of the dried polymer from the weight of the hydrogel polymer. Specifically, the water content can be defined as a value calculated by measuring the weight loss due to evaporation of moisture in the polymer in the process of drying by raising the temperature of the polymer through infrared heating. At this time, the water content is measured under the drying conditions determined as follows: the drying temperature is increased from room temperature to about 180° C. and then the temperature is maintained at 180° C., and the total drying time is set to 40 minutes, including 5 minutes for the temperature rising step.

After the monomers are subjected to a crosslinking polymerization, the base polymer powder can be obtained through steps such as drying, pulverization and classification, and through the steps such as pulverization and classification, the base polymer powder and the super absorbent polymer obtained therefrom are suitably produced and provided so as to have a particle diameter of about 150 to 850 µm. More specifically, at least 95% by weight or more of the base polymer powder and the super absorbent polymer obtained therefrom has a particle diameter of about 150 µm to 850 µm and a fine powder having a particle diameter of less than about 150 µm can contained in an amount of less than about 3% by weight.

As described above, as the particle diameter distribution of the base polymer powder and the super absorbent polymer is adjusted within the preferable range, the super absorbent polymer finally produced can exhibit excellent various physical properties.

Meanwhile, the method of drying, pulverization and classification will be described in more detail below.

In the step of forming the base polymer powder, a coarsely pulverizing step may be included before drying the hydrogel polymer in order to increase the efficiency of the drying step.

A pulverizing machine used here is not limited by its configuration, and specifically, it may include any one selected from the group consisting of a vertical pulverizer, a turbo cutter, a turbo grinder, a rotary cutter mill, a cutter mill, a disc mill, a shred crusher, a crusher, a chopper, and a disc cutter. However, it is not limited to the above-described examples.

Through the coarsely pulverizing step, the particle diameter of the hydrogel polymer can be controlled to about 0.1 to about 10 mm. Pulverizing the hydrogel polymer into a particle diameter of less than 0.1 mm is technically not easy due to its high water content, and agglomeration phenomenon between the pulverized particles may occur. Meanwhile, if the polymer is pulverized into a particle diameter of greater than 10 mm, the effect of increasing the efficiency in the subsequent drying step may be insignificant.

The hydrogel polymer coarsely pulverized as above or the hydrogel polymer immediately after polymerization without the coarsely pulverizing step is subjected to a drying step. In this case, the drying temperature of the drying step may be about 50° C. to about 250° C.

When the drying temperature is less than about 50° C., it is likely that the drying time becomes too long or the physical properties of the super absorbent polymer finally formed is deteriorated, and when the drying temperature is higher than about 250° C., only the surface of the polymer is excessively dried, and thus it is likely that fine powder is generated during the subsequent pulverizing step, and the physical properties of the super absorbent polymer finally formed is deteriorated.

Meanwhile, the drying time may be about 20 minutes to about 15 hours, in consideration of the process efficiency and the like, but it is not limited thereto.

In the drying step, the drying method may also be selected and used without being limited by its constitution if it is a method commonly used for drying the hydrogel polymer. Specifically, the drying step may be carried out by a method such as hot air supply, infrared irradiation, microwave irradiation or ultraviolet irradiation. After the drying step as above is carried out, the water content of the polymer may be about 0.1 to about 10% by weight.

Subsequently, the dried polymer obtained through the drying step is subjected to a pulverization step.

The polymer powder obtained through the pulverizing step may have a particle diameter of about 150 μm to about 850 μm. As a pulverizing device for pulverizing into such particle diameter, a pin mill, a hammer mill, a screw mill, a roll mill, a disc mill or a jog mill, etc. may be used, but the pulverizing device is not limited thereto.

Also, in order to control the physical properties of the super absorbent polymer powder finally commercialized after the pulverization step, a separate step of classifying the polymer powder obtained after the pulverization depending on the particle diameter may be undergone. Preferably, a polymer having a particle diameter of about 150 to about 850 μm is classified and only the polymer powder having such a particle diameter is subjected to the surface cross-linking reaction and finally commercialized. The particle diameter distribution of the base polymer powder obtained through these processes has been already explained, and thus additional explanation relating thereto will be omitted.

On the other hand, after forming the base polymer powder described above, the surface of the base polymer powder can be further cross-linked to form a surface cross-linked layer, thereby preparing a super absorbent polymer.

As the surface crosslinking agent, any surface crosslinking agent conventionally used for the preparation of a super absorbent polymer can be used without particular limitation. More specific examples thereof include at least one polyol selected from the group consisting ethylene glycol, propylene glycol, 1,3-propanediol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol; at least one carbonate-based compound selected from the group consisting of ethylene carbonate and propylene carbonate; an epoxy compound such as ethylene glycol diglycidyl ether; oxazoline compounds such as oxazolidinone; polyamine compounds; oxazoline compounds; mono-, di- or polyoxazolidinone compounds; or cyclic urea compounds; and the like.

The surface crosslinking agent can be used in an amount of about 0.01 to 3 parts by weight based on 100 parts by weight of the base polymer powder. By controlling the content range of the surface crosslinking agent within the above-mentioned range, it is possible to provide a super absorbent polymer exhibiting excellent absorption properties.

Further, in the surface cross-linking step, the surface crosslinking reaction may be performed by further adding at least one inorganic material selected from the group consisting of silica, clay, alumina, silica-alumina composite, titania, zinc oxide and aluminum sulfate, in addition to the surface crosslinking agent. These inorganic materials may be used in a powdery form or in a liquid form, and in particular, alumina powder, silica-alumina powder, titania powder, or nanosilica solution may be used. In addition, the inorganic material may be used in an amount of about 0.001 to about 2 parts by weight based on 100 parts by weight of the base polymer powder.

Further, in the surface cross-linking step, as the surface crosslinking is performed by adding a multivalent metal cation instead of the inorganic material or together with the inorganic material, the surface crosslinked structure of the super absorbent polymer may be further optimized. This is presumably because the metal cation forms a chelate with a carboxyl group (COOH) of the super absorbent polymer to further reduce a crosslinking distance.

Further, the method of adding the surface crosslinking agent is not limited in terms of its constitution. For example, a method of adding and mixing the surface crosslinking agent with the base polymer powder in a reactor, a method of spraying the surface crosslinking agent onto the base polymer powder, and a method of continuously mixing the base polymer powder and the surface crosslinking agent while providing them to a mixer that is continuously operated may be used.

When the surface crosslinking agent is added thereto, water and methanol may be further mixed therewith. When water and methanol are added thereto, there is an advantage that the surface crosslinking agent may be evenly dispersed in the base polymer powder. At this time, amounts of water and methanol to be added may be properly controlled for the purposes of inducing a uniform dispersion of the surface crosslinking agent, preventing an agglomeration phenomenon of the base polymer powder, and optimizing a surface penetration depth of the surface crosslinking agent.

The surface crosslinking reaction may be performed by heating the base polymer powder, to which the surface crosslinking agent is added, at about 100° C. or higher for about 20 minutes or more. In particular, in order to prepare the super absorbent polymer that can exhibit more excellent effects described above, the surface crosslinking step conditions may be controlled such that a maximum reaction temperature is about 100° C. to about 250° C.

The maximum reaction temperature may be maintained for about 20 minutes or more, or for about 20 minutes and 2 hour or less. Furthermore, the heat-up time from the reaction initiation temperature, for example, about 100° C. or higher, to the maximum reaction temperature may be controlled to be about 5 minutes or more, or about 5 minutes or more and 1 hour or less.

A heating means for surface crosslinking reaction is not particularly limited. The heating means used for polymerization of the monomer mixture may be used.

The super absorbent polymer obtained by the above-described preparation method uses an encapsulated foaming agent having a core-shell structure in which a thermoplastic resin surrounds the foaming agent, thereby exhibiting large surface area and excellent initial absorption capacity. Therefore, when the super absorbent polymer is used, it can provide a sanitary material such as a diaper or a sanitary napkin which can quickly absorb body fluids and impart a dry and soft touch feeling.

Advantageous Effects

The super absorbent polymer according to one embodiment of the present invention can exhibit large surface area and excellent initial absorption capacity. Therefore, when the super absorbent polymer is used, it can provide a sanitary material such as a diaper or a sanitary napkin which can quickly absorb body fluids and impart a dry and soft touch feeling.

DETAILED DESCRIPTION OF THE EMBODIMENTS

Hereinafter, the actions and effects of the present invention will be described in more detail with reference to specific Examples of the present invention. However, these Examples are for illustrative purposes only, and the scope of the invention is not intended to be limited thereby.

Preparation Example 1

Preparation of Encapsulated Foaming Agent

An encapsulated foaming agent was prepared having a core-shell structure, the core being iso-butane and the shell being formed of a copolymer of acrylate and acrylonitrile. The iso-butane was included in an amount of 25 wt % based on the total weight of the encapsulated foaming agent.

The average diameter of the encapsulated foaming agent was 13 μm. The diameter of each encapsulated foaming agent was measured as the average Feret diameter through an optical microscope. The average diameter of the encapsulated foaming agent was determined and defined as the average diameter of the encapsulated foaming agent.

0.2 g of an encapsulated foaming agent was coated onto a glass Petri dish, and then left on a hot plate preheated to 150° C. for 10 minutes. The encapsulated foaming agent was gradually expanded by heat, and this was observed with an optical microscope, and the maximum expansion ratio and the maximum expansion size of the encapsulated foaming agent in air were measured.

After heat was applied to the encapsulated foaming agent, the diameter of the top 10 wt % was measured in the order of many expanded particles and defined as the maximum expansion size. The ratio ($D_M/D_O$) of the average diameter ($D_M$) of the top 10 wt % of many expanded particles after applying heat to the average diameter ($D_O$) measured before applying heat to the encapsulated foaming agent was determined and defined as the maximum expansion ratio. The average diameter and average diameter all were measured in the same manner as in the diameter and average diameter of the encapsulated foaming agent.

The maximum expansion ratio of the encapsulated foaming agent in air was about 9 times, and the maximum expansion size was about 80 to 150 μm.

Preparation Example 2

Preparation of Encapsulated Foaming Agent

An encapsulated foaming agent was prepared having a core-shell structure, the core being iso-butane and the shell being formed of a copolymer of acrylate and acrylonitrile. The iso-butane was included in an amount of 25 wt % based on the total weight of the encapsulated foaming agent.

The average diameter of the encapsulated foaming agent was 15 μm, the maximum expansion ratio in air was about 9 times, and the maximum expansion size was about 90 to 180 μm.

Preparation Example 3

Preparation of Encapsulated Foaming Agent

An encapsulated foaming agent was prepared having a core-shell structure, the core being iso-pentane and the shell being formed of a copolymer of acrylate and acrylonitrile. The iso-pentane was included in an amount of 20 wt % on the total weight of the encapsulated foaming agent.

The average diameter of the encapsulated foaming agent was 40 μm, the maximum expansion ratio in air was about 12 times, and the maximum expansion size was about 400 to 540 μm.

Example 1

Preparation of Super Absorbent Polymer 100 g of acrylic acid was injected into a glass reactor, to which 123.5 g of a 32 wt % caustic soda solution was slowly added dropwise and mixed. During dropwise addition of the caustic soda solution, the temperature of the mixed solution was increased by the neutralizing heat and waited until the mixed solution was cooled. When the temperature of the mixed solution was cooled to 45° C., 0.2 g of sodium persulfate, 0.008 g of Irgacure TPO (diphenyl(2,4,6-trimethylbenzoyl)phosphine oxide), 0.3 g of the encapsulated foaming agent prepared in Preparation Example 1, 0.18 g of triethylene glycol diacrylate, 0.1 g of Cocamide monoethanolamine and 47 g of water were added to the mixed solution to prepare a monomer mixture.

The monomer mixture was fed at a feed rate of 500 to 2,000 mL/min onto a conveyor belt having a width of 10 cm and a length of 2 m and rotating at a speed of 50 cm/min. While the monomer mixture was fed, UV having an intensity of 10 mW/cm$^2$ was irradiated, and polymerization reaction was performed for 60 seconds.

The polymer obtained after the polymerization reaction was made into crumbs using a meat chopper. The crumbs were then uniformly dried in an oven capable of shifting airflow upward and downward, by flowing hot air at 185° C. from the bottom to the top for 20 minutes and again from the top to the bottom for 20 minutes. The dried product was pulverized using a pulverizer and then classified into a size of 150 to 850 μm to obtain a base polymer powder.

Thereafter, to 100 g of the base polymer powder prepared above was added a solution obtained by mixing 5.0 g of ultrapure water, 6.0 g of methanol, 0.04 g of ethylene glycol diglycidyl ether and 0.02 g of silica (trade name: Aerosil 200). After mixing for 1 minute, the surface crosslinking reaction was carried out at 180° C. for 60 minutes.

The resulting product was pulverized and classified to obtain a super absorbent polymer having a particle diameter of 150 to 850 μm.

Example 2

Preparation of Super Absorbent Polymer

A super absorbent polymer was prepared in the same manner as in Example 1, except that the encapsulated foaming agent prepared in Preparation Example 2 was used instead of the encapsulated foaming agent prepared in Preparation Example 1.

Comparative Example 1

Preparation of Super Absorbent Polymer

A super absorbent polymer was prepared in the same manner as in Preparation Example 1, except that the encapsulated foaming agent prepared in Preparation Example 1 was not added.

Comparative Example 2

Preparation of Super Absorbent Polymer

A super absorbent polymer was prepared in the same manner as in Example 1, except that $NaHCO_3$ was used instead of the encapsulated foaming agent prepared in Preparation Example 1.

Comparative Example 3

Preparation of Super Absorbent Polymer

A super absorbent polymer was prepared in the same manner as in Example 1, except that a foaming agent in which $NaHCO_3$ was encapsulated with polyethylene glycol was used instead of the encapsulated foaming agent prepared in Preparation Example 1.

Comparative Example 4

Preparation of Super Absorbent Polymer

A super absorbent polymer was prepared in the same manner as in Example 1, except that the encapsulated foaming agent prepared in Preparation Example 3 was used instead of the encapsulated foaming agent prepared in Preparation Example 1.

Test Example

Evaluation of Super Absorbent Polymer

The properties of the super absorbent polymers prepared in Examples and Comparative Examples were evaluated by the following methods, and the results are shown in Table 1 below.

(1) Initial Absorption Capacity

The initial absorption capacity of the super absorbent polymer was measured in an environment similar to the environment in which the diaper absorbs the infant's urine.

Specifically, $W_0$ (g, about 0.2 g) of the polymer was uniformly put in a nonwoven fabric-made bag and sealed. Then, the bag was immersed in 0.9 wt % of sodium chloride aqueous solution (physiological saline solution) at 36° C. After 1 minute, the bag was lifted, the physiological saline solution kept in the bag for 1 minute was allowed to drop by gravity, and then the weight $W_2(g)$ of the bag was measured. Meanwhile, the same procedure was carried out by using an empty bag not containing the polymer, and then the resultant weight $W_1(g)$ was measured.

Using the respective weights thus obtained, the initial absorption capacity was confirmed according to the following Calculation Formula 1:

$$\text{Initial absorption capacity (g/g)} = [W_2(g) - W_1(g)]/W_0(g) - 1 \quad \text{[Calculation Formula 1]}$$

in Calculation Formula 1, $W_0(g)$ is an initial weight (g) of the polymer, $W_1(g)$ is a weight of a nonwoven fabric-made empty bag not containing the polymer, which is measured after immersing the empty bag not containing the polymer in a physiological saline solution at 36° C. for 1 minute, and then dehydrating the same by gravity for 1 minute, and $W_2(g)$ is a weight of a nonwoven fabric-made bag containing the polymer, which is measured after immersing and absorbing the bag containing the polymer in a physiological saline solution at 36° C. for 1 minute, and then dehydrating the same by gravity for 1 minute.

(2) Centrifuge Retention Capacity (CRC)

The centrifuge retention capacity (CRC) for a physiological saline solution was measured in accordance with EDANA (European Disposables and Nonwovens Association) recommended test method No. NWSP 241.0.R2.

Specifically, $W_0$ (g, about 0.2 g) of the polymer was uniformly put in a nonwoven fabric-made bag and sealed. Then, the bag was immersed in 0.9 wt % of sodium chloride aqueous solution (physiological saline solution) at room temperature. After 30 minutes, water was removed from the bag by centrifugation at 250 G for 3 minutes, and the weight $W_4(g)$ of the bag was then measured. Meanwhile, the same procedure was carried out without using the polymer, and then the resultant weight $W_3(g)$ was measured.

Using the respective weights thus obtained, the centrifuge retention capacity was confirmed according to the following Formula 2:

$$CRC (g/g) = \{[W_4(g) - W_3(g)]/W_0(g)\} - 1 \quad \text{[Formula 2]}$$

in Formula 2, $W_0(g)$ is an initial weight (g) of the polymer, $W_3(g)$ is a weight of a nonwoven fabric-made empty bag not containing the polymer, which is measured after immersing the empty bag not containing the polymer in a physiological saline solution at room temperature for 30 minutes and then dehydrating the same by using a centrifuge at 250 G for 3 minutes, and $W_4(g)$ is a weight of a nonwoven fabric-made bag including the polymer, which is measured after immersing and absorbing the bag containing the polymer in a physiological saline solution at room temperature for 30 minutes and then dehydrating the same by using a centrifuge at 250 G for 3 minutes.

TABLE 1

|  | CRC [g/g] | Initial Absorption capacity [g/g] |
|---|---|---|
| Example 1 | 37.9 | 47.3 |
| Example 2 | 37.5 | 46.2 |
| Comparative Example 1 | 37.3 | 23.7 |
| Comparative Example 2 | 38.7 | 27.2 |
| Comparative Example 3 | 39.4 | 28.4 |
| Comparative Example 4 | 38.2 | 27.7 |

Referring to Table 1, it is confirmed that in Examples 1 and 2, as a super absorbent polymer is prepared using a foaming agent capable of expanding to a proper size, very excellent initial absorption capacity is exhibited.

It is also confirmed that in the case of not using an encapsulated foaming agent, or using a conventional carbonate foaming agent, or using an encapsulated foaming agent that expands too large, as in Comparative Examples 1, 2 and 4, proper pores are not formed on the surface of the super absorbent polymer particles, and thus good initial absorption capacity is not exhibited.

It is confirmed that in the case of the foaming agent in which carbonate is encapsulated with polyethylene glycol as in Comparative Example 3, polyethylene glycol stabilizes the carbonate and only delay the foaming time and does not expand to a desired size, whereby pores of a desired size are not formed on the surface of the super absorbent polymer particles and excellent initial adsorption capacity is not exhibited.

The invention claimed is:

1. A super absorbent polymer comprising:
a base polymer powder including an internally cross-linked polymer obtained by internal crosslinking polymerization of a water-soluble ethylenically unsaturated monomer having an acidic group of which at least a part is neutralized in the presence of an internal cross-linking agent and an encapsulated foaming agent; and
a surface cross-linked layer formed by surface cross-linking the internally cross-linked polymer of the base polymer powder,
wherein an initial absorption capacity of the super absorbent polymer, calculated according to the following Calculation Formula 1 is at least 30 g/g, Initial absorption capacity (g/g)= $[W_2(g)-W_1(g)]/W_0(g)-1$    [Calculation Formula 1]

wherein in Calculation Formula 1,
$W_0(g)$ is an initial weight(g) of the super absorbent polymer,
$W_1(g)$ is a weight of a nonwoven fabric-made empty bag not containing the super absorbent polymer, which is measured after immersing the empty bag not containing the super absorbent polymer in a physiological saline solution at 36° C. for 1 minute, and then dehydrating the empty bag by gravity for 1 minute, and
$W_2(g)$ is a weight of a nonwoven fabric-made bag containing the super absorbent polymer, which is measured after immersing and absorbing the bag containing the polymer in a physiological saline solution at 36° C. for 1 minute, and then dehydrating the same by gravity for 1 minute,
wherein the encapsulated foaming agent has a structure including a core containing hydrocarbon and a shell surrounding the core and formed of a thermoplastic resin, and has a maximum expansion size in air of 20 to 190 μm,
wherein the encapsulated foaming agent has an expansion ratio in air of 5 to 15 times.

2. The super absorbent polymer according to claim 1, wherein the super absorbent polymer has a centrifuge retention capacity (CRC) for a physiological saline solution of 30 to 45 g/g.

3. The super absorbent polymer according to claim 1, wherein the super absorbent polymer has an initial absorption capacity calculated according to Calculation Formula 1 of 40 to 60 g/g, and a centrifuge retention capacity (CRC) for a physiological saline solution of 35 to 40 g/g.

4. The super absorbent polymer according to claim 1, wherein the encapsulated foaming agent has an average diameter of 5 to 50 μm.

5. The super absorbent polymer according to claim 1, wherein the hydrocarbon is at least one selected from the group consisting of n-propane, n-butane, iso-butane, cyclobutane, n-pentane, iso-pentane, cyclopentane, n-hexane, iso-hexane, cyclohexane, n-heptane, iso-heptane, cycloheptane, n-octane, iso-octane, and cyclooctane.

6. The super absorbent polymer according to claim 1, wherein the thermoplastic resin is a polymer formed from at least one monomer selected from the group consisting of (meth)acrylate, (meth)acrylonitrile, aromatic vinyl, vinyl acetate, vinyl halide and vinylidene halide.

7. A sanitary material comprising the super absorbent polymer of claim 1.

8. The sanitary material according to claim 5, wherein the sanitary material is a diaper or a sanitary napkin.

* * * * *